(12) United States Patent
Tsugita (10) Patent No.: US 6,168,579 B1
(45) Date of Patent: Jan. 2, 2001

(54) FILTER FLUSH SYSTEM AND METHODS OF USE

(75) Inventor: Ross S. Tsugita, Mountain View, CA (US)

(73) Assignee: SciMed Life Systems, Inc., Maple Grove, MN (US)

(*) Notice: Under 35 U.S.C. 154(b), the term of this patent shall be extended for 0 days.

(21) Appl. No.: 09/369,052

(22) Filed: Aug. 4, 1999

(51) Int. Cl.$^7$ .................................................. A61M 29/00
(52) U.S. Cl. ...................... 604/96.01; 604/104; 604/500; 604/509; 606/200
(58) Field of Search ................................ 604/96.01, 104, 604/105, 106, 107, 500, 508, 509, 523, 532; 606/191, 194, 198, 200

(56) References Cited

U.S. PATENT DOCUMENTS

| | | | |
|---|---|---|---|
| 4,873,978 | * | 10/1989 | Ginsburg . |
| 5,053,008 | * | 10/1991 | Bajaj . |
| 5,224,953 | * | 7/1993 | Morgentaler . |
| 5,330,484 | * | 7/1994 | Gunther .............................. 606/128 |
| 5,423,742 | * | 6/1995 | Theron .................................. 604/28 |
| 5,662,671 | * | 9/1997 | Barbut et al. . |
| 5,749,848 | * | 5/1998 | Jang et al. . |
| 5,769,816 | * | 6/1998 | Barbut et al. . |
| 5,910,154 | * | 6/1999 | Tsugita et al. . |
| 5,925,060 | * | 7/1999 | Forber ................................... 606/191 |

FOREIGN PATENT DOCUMENTS

| | | | |
|---|---|---|---|
| 34 17 738 | * | 11/1985 | (DE) . |
| 0533511A1 | * | 3/1993 | (EP) . |
| WO98/39046 | * | 9/1998 | (WO) . |
| WO99/22673 | * | 5/1999 | (WO) . |

OTHER PUBLICATIONS

Jordan, Jr. et al., *Cardiovascular Surgery* 7(1):33–38 (1999).*
Marache et al., *American Heart Journal* 125(2 Pt 1):362–366 (1993).*
Nakanishi et al., *Rinsho Kyobu Geka* 14(2):110–114 (1994).*
Onal et al., *Cardiovascular Interventional Radiology* 21(5):386–392 (1998).*
Waksman et al., *American Heart Journal* 129(3):430–435 (1995).*

* cited by examiner

*Primary Examiner*—John D. Yasko
(74) *Attorney, Agent, or Firm*—Crompton, Seager & Tufte, LLC (57) ABSTRACT

A filter flush system for temporary placement of a filter in an artery or vein is disclosed. The system typically includes a guidewire insertable within a guiding catheter, which has an occlusion balloon disposed about its distal end. The guidewire has an expandable filter, which can be collapsed to pass through a lumen and distal port of the guiding catheter. The lumen is adapted to receive a variety of endovascular devices, including angioplasty, atherectomy, and stenting catheters. Fluid medium or blood can be infused through the lumen of the guiding catheter to flush embolic material or mobile plaque generated during the endovascular procedures toward the expanded filter deployed downstream from the region of interest. Methods of using the filter flush system to entrap and remove embolic material from the vessel are also disclosed.

20 Claims, 5 Drawing Sheets

FILTER FLUSH SYSTEM AND METHODS OF USE

FIELD OF THE INVENTION

The present invention relates generally to devices and methods useful in capturing embolic material in blood vessels. More specifically, the devices and methods provide a vessel filtering system for temporary deployment in arteries such as the carotid arteries and the aorta, and veins such as the subclavian vein and the superior vena cava. The system also includes a guidewire for directing endovascular devices, e.g., atherectomy, stent-deployment, or angioplasty catheters, to a region of interest and a guiding catheter with fluid flushing capability to assist in filtering.

BACKGROUND OF THE INVENTION

Treatment of thrombotic or atherosclerotic lesions in blood vessels using the endovascular approach has recently been proven to be an effective and reliable alterative to surgical intervention in selected patients. For example, directional atherectomy and percutaneous translumenal coronary angioplasty (PTCA) with or without stent deployment are useful in treating patients with coronary occlusion. Atherectomy physically removes plaque by cutting, pulverizing, or shaving in atherosclerotic arteries using a catheter-deliverable endarterectomy device. Angioplasty enlarges the lumenal diameter of a stenotic vessel by exerting mechanical force on the vascular walls. In addition to using the angioplasty, stenting, and/or atherectomy on the coronary vasculature, these endovascular techniques have also proven useful in treating other vascular lesions in, for example, carotid artery stenosis, peripheral arterial occlusive disease (especially the aorta, the iliac artery, and the femoral artery), renal artery stenosis caused by atherosclerosis or fibromuscular disease, superior vena cava syndrome, occlusion iliac vein thrombosis resistant to thrombolysis.

It is well recognized that one of the complications associated with endovascular techniques is the dislodgment of embolic materials generated during manipulation of the vessel, thereby causing occlusion of the narrower vessels downstream and ischemia or infarct of the organ which the vessel supplies. In 1995, Waksman et al. disclosed that distal embolization is common after directional atherectomy in coronary arteries and saphenous vein grafts. See Waksman et al., American Heart Journal 129(3): 430–5 (1995), incorporated herein by reference. This study found that distal embolization occurs in 28% (31 out of 111) of the patients undergoing atherectomy. In January 1999, Jordan, Jr. et al. disclosed that treatment of carotid stenosis using percutaneous angioplasty with stenting procedure is associated with more than eight times the rate of microemboli seen using carotid endarterectomy. See Jordan, Jr. et al. Cardiovascular surgery 7(1): 33–8 (1999), incorporated herein by reference. Microemboli, as detected by transcranial Doppler monitoring in this study, have been shown to be a potential cause of stroke. The embolic materials include calcium, intimal debris, atheromatous plaque, thrombi, and/or air.

There are a number of devices designed to provide blood filtering for entrapment of vascular emboli. The vast majority of these devices are designed for permanent placement in veins to prevent pulmonary embolism. A temporary venous filter device is disclosed in Bajaj, U.S. Pat. No. 5,053,008 (this and all other references cited herein are expressly incorporated by reference as if fully set forth in their entirety herein). The Bajaj device is an intracardiac catheter for temporary placement in the pulmonary trunk of a patient predisposed to pulmonary embolism due to, e.g., hip surgery, major trauma, major abdominal or pelvic surgery, or immobilization. The Bajaj device includes an umbrella made from meshwork which traps venous emboli before they reach the lungs. This device is designed for venous filtration and is not suitable for arterial use because of the hemodynamic differences between arteries and veins.

There are very few intravascular devices designed for arterial use. Arteries are much more flexible and elastic than veins and, in the arteries, blood flow is pulsatile with large pressure variations between systolic and diastolic flow. These pressure variations cause the artery walls to expand and contract. Blood flow rates in the arteries vary from about 1 to about 5 L/min. Ginsburg, U.S. Pat. No. 4,873,978, discloses an arterial filtering system, which includes a catheter with a strainer device at its distal end. This device is inserted into the vessel downstream from the treatment site and, after treatment, the strainer is collapsed around the entrapped emboli and removed from the body. The Ginsburg device could not withstand flow rates of 5 L/min. It is designed for only small arteries and therefore could not capture emboli destined for all parts of the body. Ing. Walter Hengst GmbH & Co, German Patent DE 34 17 738, also discloses another arterial filter having a folding linkage system which converts the filter from the collapsed to the expanded state.

Filters mounted to the distal end of guidewires have been proposed for intravascular blood filtration. A majority of these devices includes a filter which is attached to a guidewire and is mechanically actuated via struts or a pre-shaped basket which deploy in the vessel. These filters are typically mesh "parachutes" which are attached to the shaft of the wire at the distal end and to wire struts which extend outward in a radial direction on the proximal end. The radial struts open the proximal end of the filter to the wall of the vessel. Blood flowing through the vessel is forced through the mesh thereby capturing embolic material in the filter. A major disadvantage associated with these filter devices is that the filters generally rely on vascular blood flow to push debris into the filters. If blood flow in the vessel becomes restricted, the loosely attached embolic material may not be subjected to normal turbulent blood flow. The embolic particles may stay in the vessel proximal to the filter until the higher normal flow is re-established (i.e., when the filter is removed), thereby reducing the efficacy of the filtering devices.

Another means of removing embolic material utilizes temporary occlusion devices, such as balloon occlusion catheters and vascular clamps, to isolate a section of a vessel. After blood flow is isolated in the vessel, fluid or blood within the vessel is aspirated to remove embolic debris. One of the disadvantages associated with occlusion devices is that they require temporary cessation or reduction in distal perfusion that may affect oxygenation of distal organs. Shunts may be placed distal to the devices to maintain perfusion to distal organs. However, insertion of the shunts creates additional trauma to the vessel and may generate additional embolic material.

What is needed are simple and safe blood filtering devices which can be temporarily placed in the arteries and veins and can be used with endovascular instruments to effectively prevent distal embolization. Existing devices are inadequate for this purpose.

SUMMARY OF THE INVENTION

Fixed or mobile plaque present in the aorta can dislodge and cause renal infarct or ischemia to other organs. The build up of plaque in the carotid arteries also poses a risk of ischemic stroke by embolization and presents an additional threat of reducing blood flow by occluding the vessel lumen. Plaque present in the iliac and femoral arteries may cause ischemia of the lower extremities, either through distal embolization of atheromatous material or through in situ stenosis of the diseased blood vessel, i.e., narrowing of lumenal diameter. Atherectomy or angioplasty with or without stent deployment in these vessels prevents the above disease from occurring, but can also create these conditions unless the device is specially designed to capture embolic material dislodged during the procedure.

The present invention provides devices and methods for temporary placement of blood filtering capabilities in an artery or vein during endovascular procedures. More specifically, the invention provides a filter flush system which accommodates insertion of endovascular catheters for removing atherosclerotic plaques and/or thrombi and enlarging the lumenal diameter of a stenotic vessel. The filter system also provides means for maintaining distal perfusion during isolation of blood flow, and for pushing embolic debris into the filter during a low-flow state, thereby enhancing filtering capabilities.

In one embodiment, the filter flush system includes an expandable filter, e.g., a parachute, basket, or scroll, mounted on a distal end of a guidewire, and a large diameter catheter (such as a guiding catheter, angiographic catheter, introducer sheath, vessel dilators) having a lumen communicating with a proximal end and a port at its distal end. The distal end of the catheter is adapted for insertion into an artery or vein. The proximal end of the catheter may include a hemostatic valve. An expandable occluder, which may comprise an elastomeric balloon, is disposed about the distal end of the guiding catheter and communicates with an inflation lumen for providing isolation of blood flow in the vessel. The lumen of the catheter is adapted to receive the guidewire, which passes through the distal port. A proximal end of the guidewire will typically be operable from outside the proximal end of the catheter for manipulation of the guidewire independently of the catheter. The lumen of the catheter is also adapted to receive an endovascular device, e.g., an angioplasty, stent-deployment, or atherectomy catheter.

The endovascular catheters typically include a proximal end, a distal end and a lumen which receives the guidewire. An excising member, e.g., a cutting blade, abrasive member, wire cutter, jaws, claws, pincher, snare, etc., is included at the distal region of an atherectomy catheter. An expandable balloon is included at a distal region of an angioplasty catheter. An expandable stent is mounted at a distal region of a stent-deployment catheter. The atherectomy catheter may optionally further include means for intravascular imaging, e.g., an ultrasonic transducer. In certain embodiments, the angioplasty catheters include a stent disposed about the balloon at their distal region. Intravascular imaging devices and stents are fully described in the art and will not be further discussed here.

In another embodiment, the expandable filter comprises an expansion frame and a mesh disposed over the frame. In certain embodiments, the frame comprises a plurality of struts bonded to the guidewire at a first end, and the struts expand radially outward at a second end. The frame may comprise an inflation seal for providing better contact with the vascular walls. The construction and use of expansion means and associated filter mesh have been thoroughly discussed in earlier applications including Barbut et al., U.S. application Ser. No. 08/533,137, filed Nov. 7, 1995, Barbut et al., U.S. application Ser. No. 08/580,223, filed Dec. 28, 1995, Barbut et al., U.S. application Ser. No. 08/584,759, filed Jan 9, 1996, Barbut et al., U.S. application Ser. No. 08/640,015, filed Apr. 30 1996, Barbut et al., U.S. application Ser. No. 08/645,762, filed May 14, 1996, and, Barbut et al., U.S. Pat. No. 5,662,671, and the contents of each of these prior applications are expressly incorporated herein by reference.

In still another embodiment, the guiding catheter includes an infusion port proximal to the occlusion balloon. The port communicates with an infusion lumen in the catheter and is adapted for infusion of fluid or pharmaceutical agents. Using the infusion port, the dosage of pharmaceutical agent required to achieve local effect can be reduced compared to administration by systemic route. Side effects, e.g., hemorrhage associated with systemic administration of t-PA, can also be minimized. In certain embodiments, the angioplasty catheter may include an infusion port proximal to the angioplasty balloon and a perfusion port distal to the balloon. The infusion and perfusion port communicate, respectively, with an infusion and perfusion lumen included in the angioplasty catheter. The infusion port is adapted for aspiration of fluid, blood, air, or vascular debris.

The methods of the present invention include protecting a patient from embolization during an endovascular procedure to remove plaque and/or thrombi from the coronary artery, aorta, common carotid artery, external and internal carotid arteries, brachiocephalic trunk, middle cerebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery, and all other arteries carrying oxygenated blood. The methods also include prevention of distal embolization during an endovascular procedure to remove thrombi and/or foreign bodies in the venous circulation, including the superior vena cava, inferior vena cava, external and internal jugular veins, brachiocephalic vein, pulmonary artery, subclavian vein, brachial vein, axillary vein, iliac vein, renal vein, femoral vein, profunda femoris vein, great saphenous vein, portal vein, splenic vein, hepatic vein, and azygous vein.

In a first method of using the filter flush system, the distal end of the guidewire, having the filter in a collapsed state, is inserted through an artery or vein. The filter and the distal region of the guidewire are positioned in the vessel beyond a region of interest, followed by expansion of the filter. The guiding catheter is inserted over the guidewire, and the occlusion balloon is positioned proximal to the region of interest. The distal region of an atherectomy, stent-deployment, or angioplasty catheter is inserted over the guidewire, where the guidewire is carried within the lumen of the guiding catheter, and advanced to the region of interest. The occlusion balloon is then expanded to isolate blood flow in the vessel while the endovascular catheter removes or otherwise treats the stenotic lesion in the vascular lumen. The catheter may then be withdrawn or left in place, and fluid or blood is infused through the lumen of the guiding catheter to flush embolic debris into the expanded filter. In certain embodiments, the fluid is directed as a jet toward the atheroma for the purpose of blasting the atheroma from the wall of the vessel and thereafter into the filter. The steps of inserting the endovascular catheter and infusing fluid to flush embolic debris may be repeated until an adequate lumenal diameter is established. The filter is then collapsed and removed, together with the captured embolic debris, from the vessel by withdrawing the guidewire. The guiding catheter is withdrawn after the occlusion balloon is deflated.

In another method, after the expanded filter and the guiding catheter are positioned, respectively, in a vessel distal to and proximal from the region of interest, the angioplasty balloon carried by the angioplasty catheter is inflated to dilate the stenotic vascular lumen. Blood, fluid, air, and/or embolic debris present between the occlusion and angioplasty balloon may be aspirated. Alternatively, the occlusion balloon may be deflated during the inflation of the angioplasty balloon to allow blood to be aspirated from the proximal port and passed to the perfusion port distal to the angioplasty balloon, thereby maintaining perfusion to the distal organs during angioplasty.

It will be understood that there are several advantages in using the devices and methods disclosed herein for capturing and removing embolic debris during endovascular procedures. For example, the filter flush system (1) is particularly suited for temporary filtration of blood in any vessel to entrap embolic debris, thereby minimizing neurologic, cognitive, and cardiac complications associated with distal embolization, (2) can withstand high arterial blood flow for an extended time, (3) includes a mesh that is porous enough to allow adequate blood flow in a blood vessel while capturing mobile emboli, (4) is adapted to accommodate an endovascular catheter with or without imaging device, (5) may remove mobile plaque in a vessel by flushing through the guiding catheter, (6) provides means to maintain perfusion to distal organs during endovascular procedures, (7) provide means to administer pharmaceutical agents, e.g., tissue plasminogen activator or nitroglycerin, locally to the region of interest, thereby minimizing side effects associated with systemic administration, and (8) can be used in adult and pediatric patients.

DETAILED DESCRIPTION

Figure 1A:
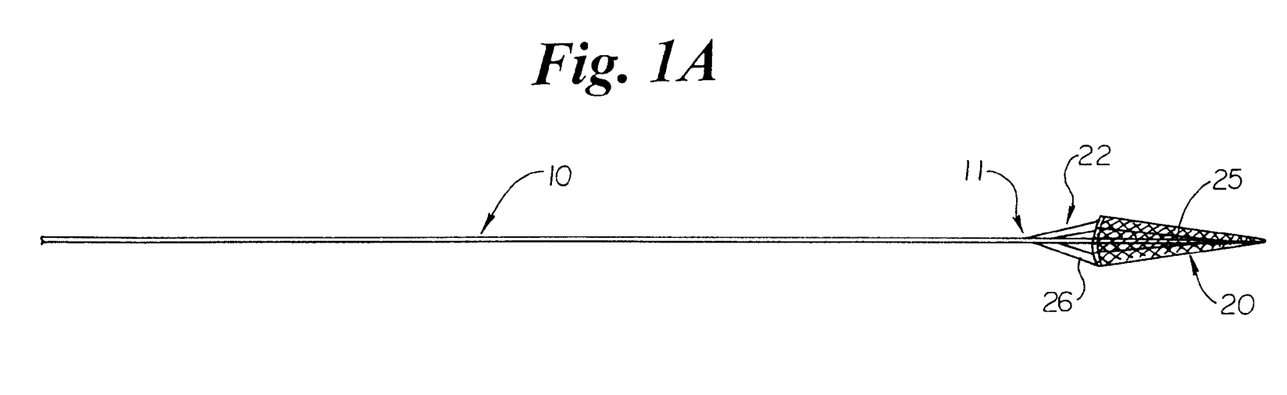
FIG. 1A depicts an embodiment of a collapsed filter mounted on a distal region of a guidewire according to the present invention.
Figure 1B:
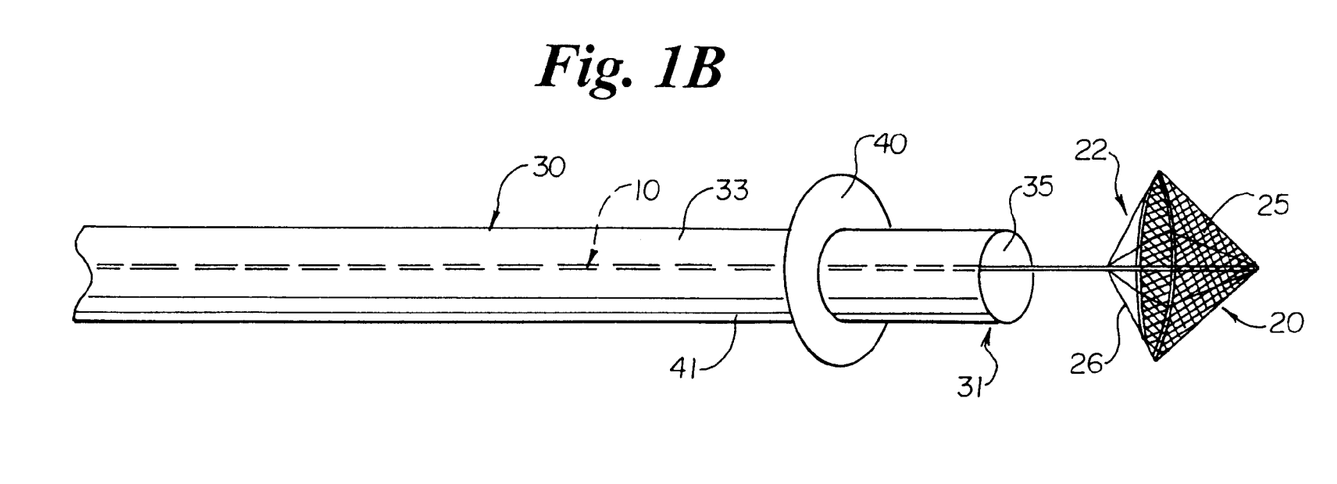
FIG. 1B depicts the guidewire and expanded filter of FIG. 1A inserted through a lumen of a guiding catheter.

In a first embodiment, a filter system for temporary placement in a vessel, either an artery or vein, is provided as depicted in FIGS. 1A and 1B. The filter system includes guidewire 10 having a proximal end, distal end 11, and expandable filter 20 mounted at the distal end. The filter comprises umbrella frame 22 and mesh 25 which is sonic welded or adhesive bonded to arms 26 of the umbrella frame. Anticoagulants, such as heparin and heparinoids, may be applied to mesh 25 to reduce thrombi formation on the mesh. The filter can be collapsed as shown in FIG. 1A to facilitate insertion into a vessel, and thereafter expanded as shown in FIG. 1B. A variety of suitable filter guidewires for use herein are described in Tsugita et al., U.S. Pat. No. 5,910,154, which is incorporated herein by reference in its entirety.

The filter system also includes guiding catheter 30 having lumen 33 communicating with a proximal end and distal end 31, and occlusion balloon 40 disposed about the distal end. Balloon 40 communicates with inflation lumen 41, which is adapted to receive fluid or air for expansion of the balloon. Lumen 33 of the catheter communicates with distal port 35 and is adapted to receive guidewire 10 and other endovascular devices, such as atherectomy catheters, endovascular imaging devices, stent-deployment catheters, angioplasty catheters, pressure monitors, electrophysiology catheters, and aspirators.

Figure 2A:
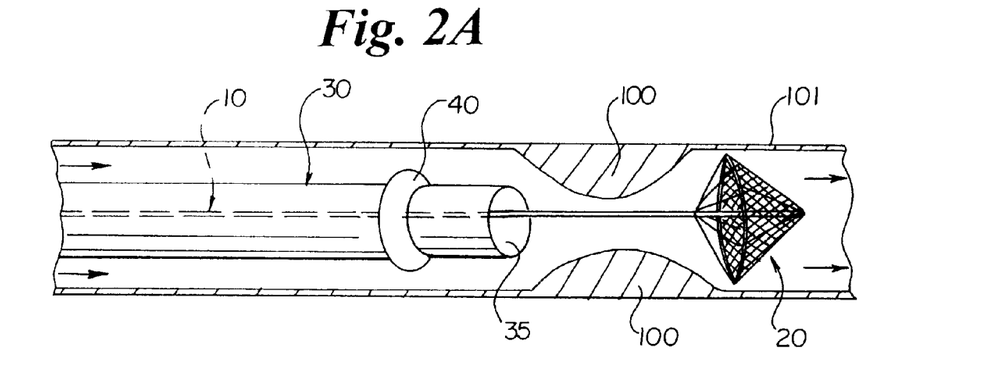
FIG. 2A depicts the filter system of FIG. 1B inserted into a vessel.
Figure 2B:
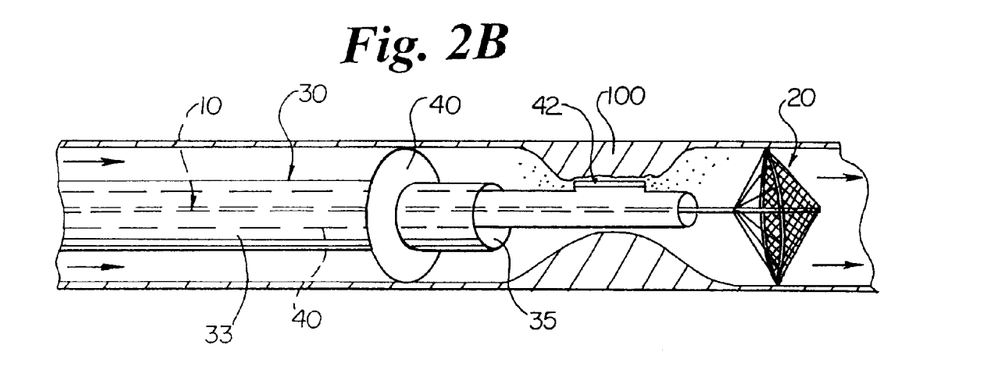
FIG. 2B depicts an atherectomy catheter inserted through the lumen of the guiding catheter of FIG. 2A.
Figure 2C:
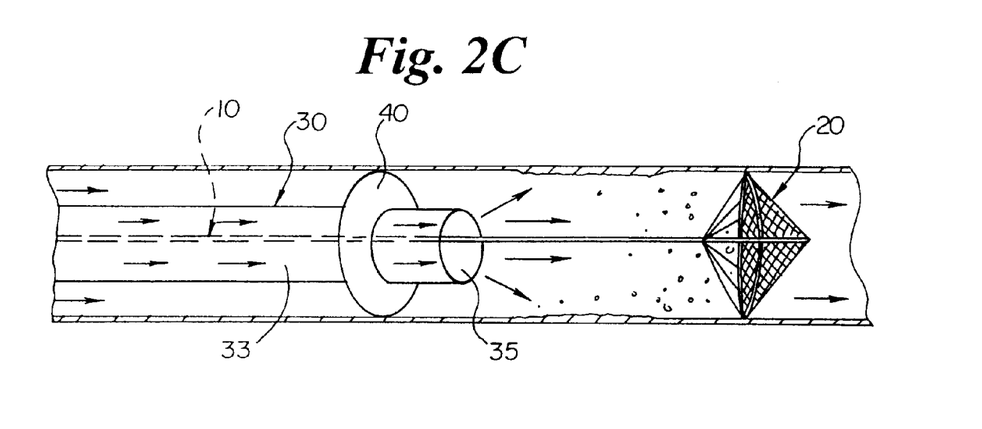
FIG. 2C depicts the filter system of FIG. 2A capturing embolic debris.

In use, as depicted in FIGS. 2A, 2B, and 2C, filter 20 (in the collapsed condition) and distal end 11 of the guidewire is inserted percutaneously through a peripheral artery or vein typically in the direction of blood flow (however, it is contemplated that guidewire 10 may be inserted in a direction opposite the blood flow). Filter 20 is advanced distal to atheromatous plaque 100 and expanded to contact the vessel walls 101 as depicted in FIG. 2A. Guiding catheter 30 is then inserted over guidewire 10 until distal port 35 is positioned proximal to plaque 100. Atherectomy catheter 40, having atherectomy device 42 mounted on a distal region, is inserted within lumen 33 of the catheter and over guidewire 10. Atherectomy device 42 is advanced distal to port 35 of the catheter to a position adjacent plague 100. Occlusion balloon 40 is inflated to isolate blood flow in the vessel, while atherectomy device 42 removes plaque 100 as depicted in FIG. 2B.

After adequate lumenal size is achieved by atherectomy, occlusion balloon 40 is deflated, allowing blood flow to be re-established in the region of interest to push the embolic material generated during the procedure toward filter 20 and to perfuse distal organs. Occlusion balloon 40 can be re-inflated to isolate blood flow for repeat atherectomy or other endovascular procedure, e.g., aspiration. After completion of the procedure, the atherectomy catheter is withdrawn from guiding catheter 30 as depicted in FIG. 2C. Fluid or blood is infused through lumen 33 of the guiding catheter to flush the embolic material not cleared as a result of low-flow state toward filter 20. This may be done with or without balloon 40 deployed. The fluid flush may also be directed at the vessel wall to blast free loosely held atheromatous material which remains after atherectomy. In certain cases, the filter may become loaded with excessive amounts of material. In this case, it may be desirable to deploy a separate aspiration catheter through the guiding catheter to extend distally to the filter, and thereby operate to suction embolic material captured in the mesh. Guiding catheter 30 is removed from the vessel. Filter 20 with the captured embolic debris is collapsed and removed from the vessel by withdrawing guidewire 10. The guidewire may alternatively be withdrawn into guide catheter 30, and both devices thereafter simultaneously withdrawn. In another embodiment, the guidewire may have a separate capture sheath to assist in its placement and removal by pulling the guidewire into the sheath prior to placement or removal.

By way of example, when the filter system as disclosed herein is intended for use in the aorta, the area of the mesh required for the device is calculated from Bernoulli's equation as described in our earlier applications including Barbut et al., U.S. application Ser. No., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. application Ser. No. 08/640,015, filed Apr. 30, 1996, and Barbut et al., and U.S. application Ser. No. 08/645,762, filed May 14, 1996, all of which are incorporated herein by reference.

In an embodiment of the filter flush system that is to be used in the aorta, mesh with dimensions within the following ranges is desirable: mesh area is 0.004–5 in$^2$, more preferably 0.007–4 in$^2$, more preferably 0.010–3 in$^2$, more preferably 0.015–2 in$^2$, more preferably 0.020–1 in$^2$, more preferably 0.025–0.076 in$^2$; mesh thickness is 60–280 $\mu$m, more preferably 70–270 $\mu$m, more preferably 80–260 $\mu$m, more preferably 90–250 $\mu$m, more preferably 100–250 $\mu$m, more preferably 120–230 $\mu$m, more preferably 140 –210 $\mu$m; thread diameter is 30–145 $\mu$m, more preferably 40–135 $\mu$m, more preferably 50–125 $\mu$m, more preferably 60–115 $\mu$m, more preferably 70–105 $\mu$m, and pore size is 500 $\mu$m or less, more preferably 400 $\mu$m or less, more preferably 300 $\mu$m or less, more preferably 200 $\mu$m or less, more preferably 100 $\mu$m or less, more preferably 50 $\mu$m or less and usually larger than at least a red blood cell. In a preferred embodiment of the invention, mesh area is 2–8 in$^2$, mesh thickness is 60–200 $\mu$m, thread diameter is 30–100 $\mu$m, and pore size is 50–300 $\mu$m. In a further preferred embodiment of the invention, mesh area is 3–5 in$^2$, mesh thickness is 60–150 $\mu$m, thread diameter is 50–80 $\mu$m, and pore size is 100–250 $\mu$m.

In other embodiments, the filter comprises a thin film laser cut with holes to allow blood flow. Typical dimensions include pore size of 20–500 $\mu$m, a thickness of 0.0005–0.003 inches, and area approximately same as for meshes described above.

Once appropriate physical characteristics are determined, suitable mesh can be found among standard meshes known in the art. For example, polyester meshes may be used, such as meshes made by Saati Corporations and Tetko Inc. These are available in sheet form and can be easily cut and formed into a desired shape. In a preferred embodiment, the mesh is sonic welded into a cone shape. Other meshes known in the art, which have the desired physical characteristics, are also suitable. Anticoagulants, such as heparin and heparinoids, may be applied to the mesh to reduce the chances of blood clotting on the mesh. Anticoagulants other than heparinoids also may be used, e.g., monoclonal antibodies such as ReoPro (Centocor). The anticoagulant may be painted or sprayed onto the mesh. A chemical dip comprising the anticoagulant also may be used. Other methods known in the art for applying chemicals to mesh may be used.

Figure 3A:
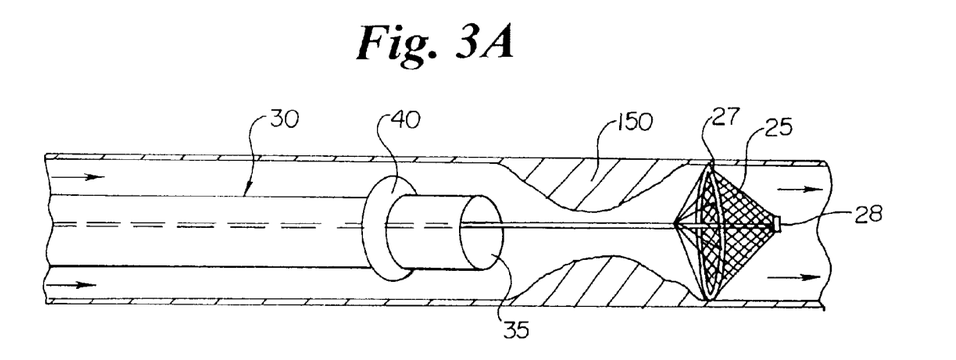
FIG. 3A depicts another embodiment of the filter system including an inflation seal on the filter.
Figure 3B:
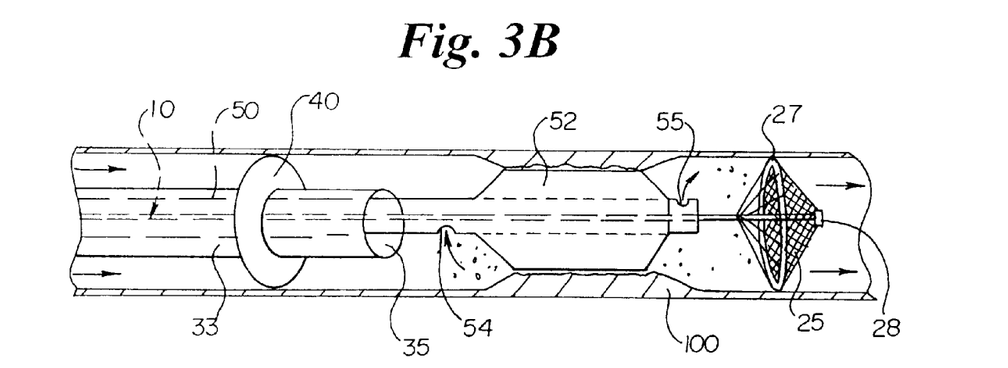
FIG. 3B depicts an angioplasty catheter inserted through the lumen of the guiding catheter of FIG. 3A.
Figure 3C:
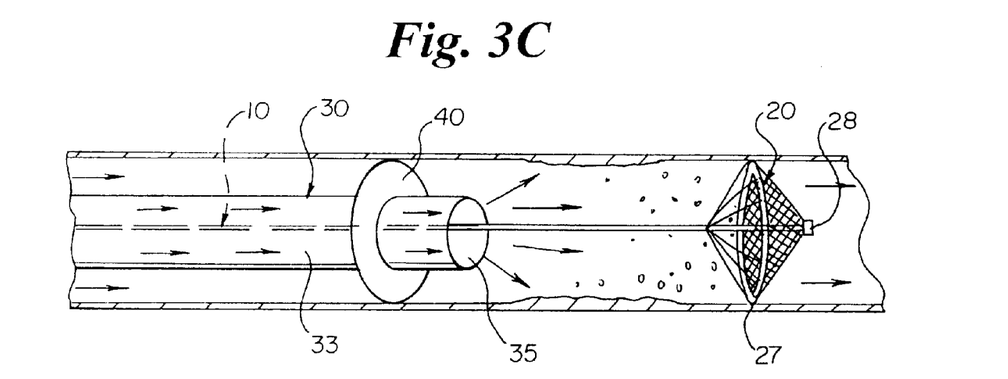
FIG. 3C depicts the filter system of FIG. 3A capturing embolic debris.

FIGS. 3A, 3B, and 3C depict another embodiment of the filter flush system for temporary placement in a vessel. Mesh 25 of filter 20 is operably connected to inflation seal 27 at a first edge and end plate 28 at a second edge. The inflation seal is expandable between a contracted condition and an enlarged condition. In use, in a contracted condition, inflation seal 27 and mesh 25 can be inserted through a peripheral vessel into a region of interest, typically distal to atheromatous plaque 100, as depicted in FIG. 3A. The inflation seal is expanded by injection of fluid or gas to achieve contact with the inner wall of vessel 101. Guiding catheter 30 is inserted over guidewire 10, and distal port 35 is positioned proximal to plaque 100.

Percutaneous translumenal angioplasty has been successful in treating arterial stenosis as well as occlusive venous thrombosis resistant to thrombolysis. See American Heart Journal 125 (2 Pt 1): 362–6 (1993). In FIG. 3B, angioplasty catheter 50, which has angioplasty balloon 52 mounted on a distal region, is inserted through lumen 33 of the guiding catheter over guidewire 10. In a deflated state, the angioplasty balloon is advanced through port 35 to a position adjacent plaque 100. The atheromatous plaque is compressed by inflating balloon 52, thereby dilating the stenosis in the vessel.

In certain embodiments, the angioplasty catheter includes infusion port 54 proximal and perfusion port 55 proximal and distal to balloon 52, respectively. Infusion port 54 may be used to administer pharmaceutical agents, e.g., t-PA or nitroglycerin and to aspirate air, thrombi, plaque, and/or tissue debris. Balloons 40 may be inflated or deflated during angioplasty. Oxygenated medium or blood may be infused through port 55 to provide perfusion to distal organs during angioplasty and facilitate flushing of embolic material into the filter.

In certain embodiments, a prosthesis, such as a stent, is closely associated with the angioplasty balloon. The stent is typically crimped onto the balloon and is capable of controlled radial expansion in a region of interest upon the application of a radial, outwardly extending force from the interior of the stent. The construction of a catheter system carrying a stent is described in detail in Jang et al., U.S. Pat. No. 5,749,848, which is incorporated herein by reference.

The angioplasty catheter may then be withdrawn from the vessel through lumen 33 of the guiding catheter after completion of angioplasty as depicted in FIG. 3C. Occlusion balloon 40 is deflated to re-establish blood flow. Before or after deflation of balloon 40, fluid or blood can be infused through lumen 33 and port 35 to flush embolic material into filter 20. After embolic material is captured and retained in the filter, guiding catheter 30 is removed from the vessel. The filter is then contracted by deflating inflation seal 27 and, with the captured embolic material, is withdrawn from the vessel and removed from the patient's body.

Figure 4A:
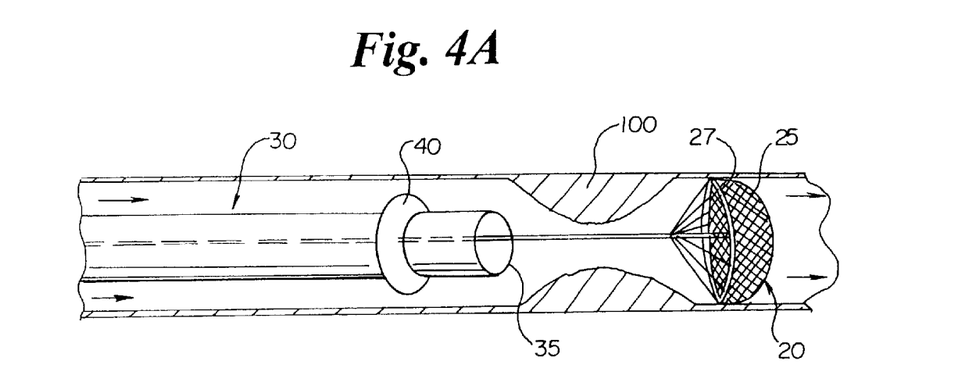
FIG. 4A depicts another embodiment of the filter system having a basket filter.
Figure 4B:
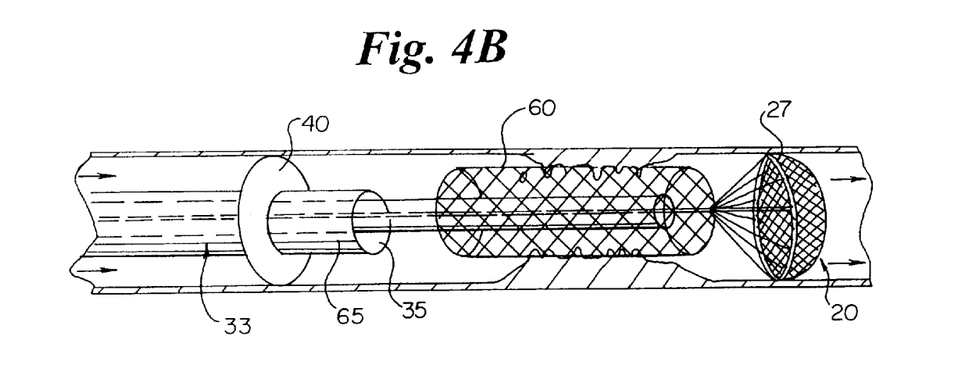
FIG. 4B depicts a stent-deployment catheter inserted through the lumen of the guiding catheter of FIG. 4A.
Figure 4C:
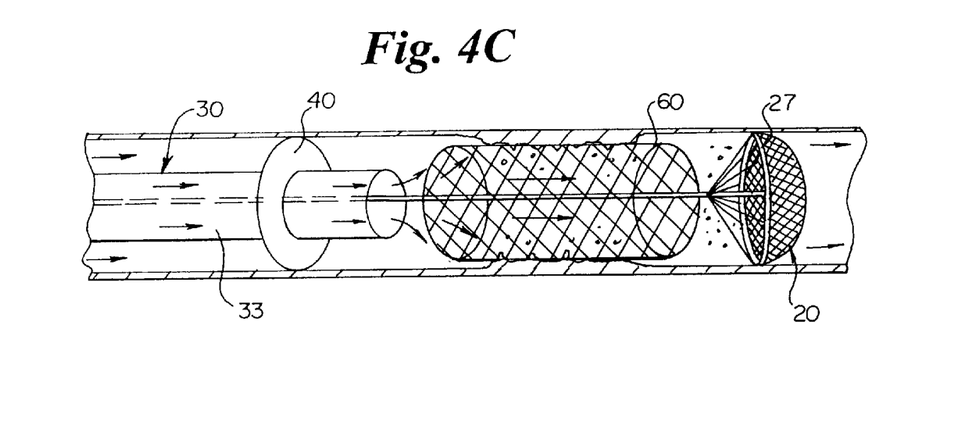
FIG. 4C depicts the filter system of FIG. 4A capturing embolic debris.

Another embodiment of the filter flush system is depicted in FIGS. 4A, 4B, and 4C. Filter 20 is in the form of a pre-shaped basket, having mesh 25 operably connected to inflation seal 27. The inflation seal can be contracted and expanded by infusing gas or fluid. In use, in a contracted condition, inflation seal 27 and mesh 25 are inserted through a peripheral vessel distal to atheromatous plaque 100 as depicted in FIG. 4A. The inflation seal is expanded to contact the inner wall of vessel 101. Guiding catheter 30 is inserted over guidewire 10, having distal port 35 positioned proximal to plaque 100.

Primary stenting for complex atherosclerotic plaque has been efficacious in treating aortic and iliac stenosis that are not amenable to balloon angioplasty. See Onal, et al., Cardiovascular Interventional Radiology 21(5): 386–92 (1998). Catheter intervention to the venous system using expandable metallic stents has been successful in treating superior vena cava syndrome which is mainly associated with malignant tumors and is resistant to any other therapy, including balloon angioplasty and surgery. See Nakanishi, et al., Rinsho Kyoby Geka 14(2): 110–4 (1994). Endovascular catheter 65, which is equipped with self-expanding stent 60 mounted on a distal region, is inserted through lumen 33 of the guiding catheter over guidewire 10 as depicted in FIG. 4B. The stent may be composed of a shape retaining metal, such as nitinol. Catheter 65 will include means for retaining the self-expanding stent. Retaining means may take the form of a sheath disposed about the distal region of the catheter so that the stent is operatively associated with and contained by the sheath, and when the sheath is removed, the stent is re eased and automatically enlarged to an expanded diameter. Plaque 100 is shown in FIGS. 4B and 4C reduced by the self-expanding and thermally activatable stent 60. The construction and deployment of a self-expanding stent is disclosed in Morgentaler, U.S. Pat. No. 5,224,953, which is expressly incorporated herein by reference.

In FIG. 4C, after stent 60 is deployed over plaque 100, endovascular catheter 65 is removed, leaving lumen 33 of guiding catheter 30 available for infusion of fluid medium. Mobile plaque, which refers to vascular deposits comprising a solidified base and a floppy projection attached to the base which can be dislodged by normal pulsating blood flow, may be found to project through the mesh of stent 60. By flushing fluid through stent 60, the mobile plaque may dislodge and be captured by filter 20. After embolic material is captured and retained in the filter, guiding catheter 30 is removed from the vessel. Filter 20 is contracted, before or after removal of the guiding catheter, by deflating inflation seal 27, and with captured embolic material, is withdrawn from the vessel and removed from the patient's body.

Figure 5:
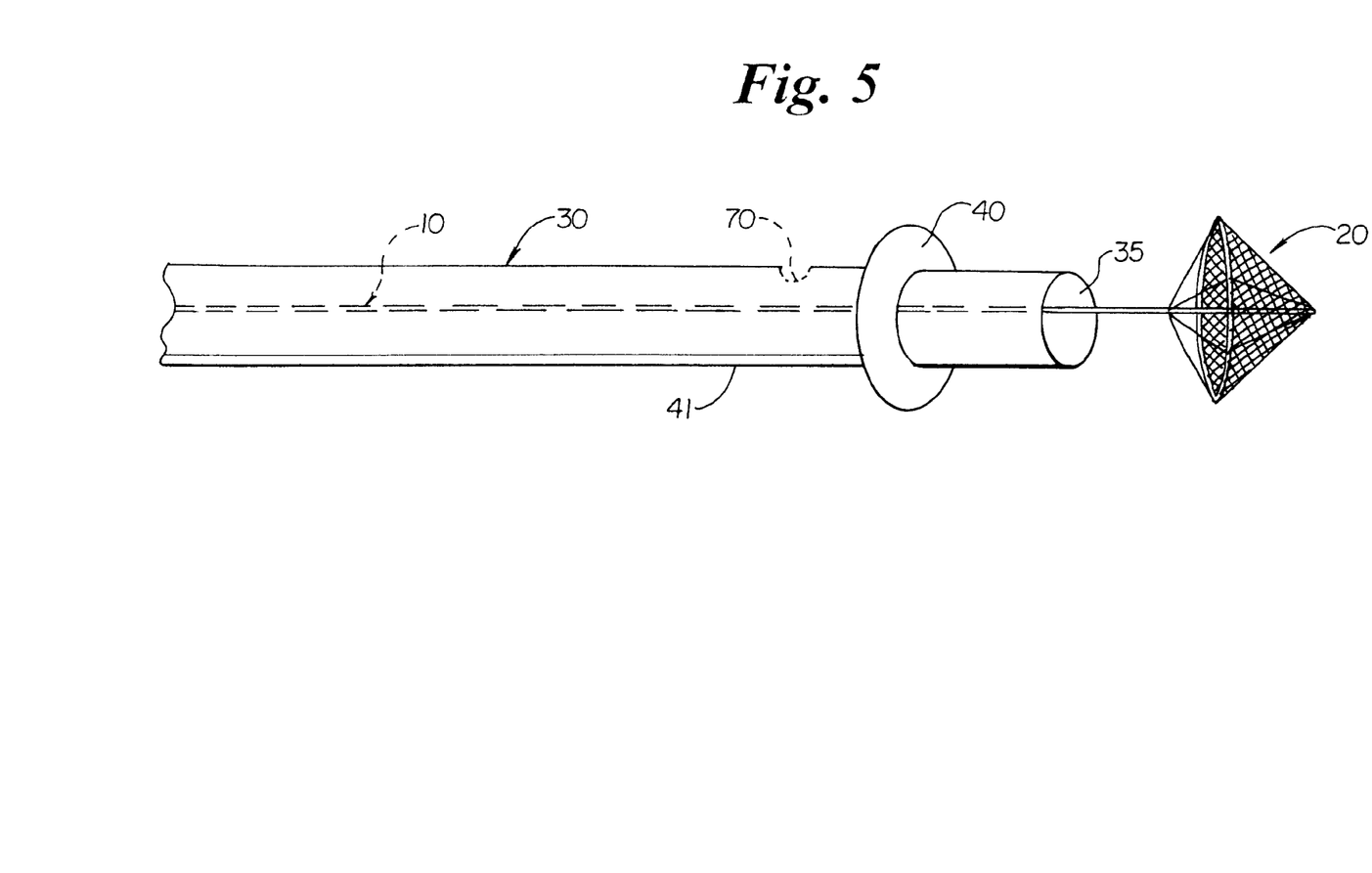
FIG. 5 depicts another embodiment of the guiding catheter having an infusion port proximal to the occlusion balloon.

FIG. 5 depicts another embodiment of the filter flush system having infusion port 70, which is located proximal to occlusion balloon 40 and communicates with lumen 33 of guiding catheter 30. Port 70 allows fluid intake and blood to flow from the proximal side of the occlusion balloon and exit distal port 35 of the catheter to provide perfusion to distal organs during an endovascular procedure. In certain embodiments, the guiding catheter may include a plurality of infusion ports proximal to the occlusion balloon, and optionally a one-way valve on the infusion port to eliminate retrograde blood flow. In certain embodiments, the guiding catheter may include aspiration port(s) distal to the occlusion balloon for aspirating vascular debris generated during the endovascular procedure.

The length of the guiding catheter and guidewire will generally be between 15 and 200 centimeters, preferably approximately between 50 and 150 centimeters. The inner diameter of the catheter lumen will generally be between 1.0 and 7 millimeters, preferably approximately between 1.5 and 2.6 millimeters. The diameter of an expanded occlusion balloon will generally be between 1.5 to 50.0 millimeters, preferably approximately between 3.0 and 8.0 millimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. For example, it will be understood that any type of expansion frame disclosed herein or in prior applications can be used with any of the therapeutic catheter interventions, even though any given figure might depict only a particular combination. Moreover, occlusion devices other than balloons can be used with any of the embodiments disclosed herein.

What is claimed is:

1. A vessel filtering system, comprising:
   a guidewire having a proximal end and a distal end;
   an expandable filter mounted at the distal end of the guidewire;
   a guiding catheter having a proximal end, a distal end, and a lumen therebetween, the lumen adapted to receive the guidewire which passes through a distal port on the guiding catheter; and
   an occlusion balloon disposed about the distal end of the guiding catheter.

2. The system of claim 1, further comprising an angioplasty catheter having a proximal end, a distal end, a lumen which receives the guidewire, and wherein the lumen of the guiding catheter is adapted to receive the angioplasty catheter.

3. The system of claim 1, wherein the expandable filter comprises an expansion frame and a mesh disposed over the frame.

4. The system of claim 3, wherein the mesh is woven.

5. The system of claim 3, wherein the mesh comprises a thin film having holes to allow fluid flow.

6. The system of claim 3, wherein the frame comprises a plurality of struts bonded to the guidewire at a first end, and which expands radially outward at a second end.

7. The system of claim 3, wherein the frame comprises an inflation seal.

8. The system of claim 1, wherein the guiding catheter includes an aspiration port distal the occlusion balloon, the aspiration port communicating with an aspiration lumen.

9. The system of claim 2, further comprising a stent disposed about the angioplasty catheter.

10. The system of claim 1, wherein the occlusion balloon communicates with an inflation lumen.

11. The system of claim 1, further comprising an atherectomy catheter having a proximal end, a distal end, a lumen which receives the guidewire, and wherein the lumen of the guiding catheter is adapted to receive the angioplasty catheter.

12. The system of claim 1, wherein the guiding catheter includes an infusion port proximal to the occlusion balloon.

13. The system of claim 12, wherein the infusion port communicates with the lumen of the guiding catheter.

14. The system of claim 2, wherein the angioplasty catheter includes an infusion port proximal to the angioplasty balloon.

15. The system of claim 14, wherein the infusion port communicates with a perfusion port distal the angioplasty balloon.

16. A method for flushing embolic debris into a filter, comprising the steps of:
   providing a guidewire having an expandable filter at a distal end;
   providing a guiding catheter having an occlusion balloon at a distal end and a lumen extending to a port at the distal end;
   inserting the guidewire into a vessel;
   advancing the expandable filter beyond a region of interest;
   expanding the filter;
   inserting the guiding catheter over the guidewire and positioning the occlusion balloon proximal the region of interest;
   expanding the occlusion balloon to occlude the vessel; and
   infusing fluid through the lumen of the guiding catheter to flush atheromatous material into the expandable filter.

17. The method of claim 16, wherein the guiding catheter is inserted over the guidewire before the step of expanding the filter.

18. The method of claim 16, wherein the guiding catheter is inserted over the guidewire before the step of advancing the expandable filter beyond the region of interest.

19. The method of claim 16, wherein the vessel is coronary artery.

20. The method of claim 16, wherein the vessel is the carotid artery.

* * * * *